United States Patent [19]

Leimgruber et al.

[11] 3,957,826
[45] May 18, 1976

[54] SPIROLACTONE PRODUCTION

[75] Inventors: Willy Leimgruber, Montclair; Manfred Weigele, North Caldwell, both of N.J.

[73] Assignee: Hoffmann-La Roche Inc., Nutley, N.J.

[22] Filed: May 23, 1975

[21] Appl. No.: 580,389

Related U.S. Application Data

[62] Division of Ser. No. 447,711, March 4, 1974, Pat. No. 3,917,646, which is a division of Ser. No. 212,790, Dec. 27, 1971, Pat. No. 3,812,181.

[52] U.S. Cl. ......................................... 260/343.3 R
[51] Int. Cl.² ........................................ C07D 493/10
[58] Field of Search ................................ 260/343.3

[56] References Cited
UNITED STATES PATENTS 3,812,181    5/1974    Leimgruber et al. ............... 260/520

Primary Examiner—James A. Patten
Attorney, Agent, or Firm—Samuel L. Welt; George M. Gould; Raymond R. Wittekind

[57] ABSTRACT

A novel class of reagents react with primary amine-containing compounds, preferably polypeptides and amino acids, to form highly fluorescent products. This reaction serves as a basis for a rapid and highly sensitive assay method for primary amine-containing compounds.

4 Claims, No Drawings

SPIROLACTONE PRODUCTION

This is a division of application Ser. No. 447,711 filed Mar. 4, 1974, now U.S. Pat. No. 3,917,646, issued Nov. 4, 1975, which is a divisional of Ser. No. 212,790, filed Dec. 27, 1971, now U.S. Pat. No. 3,812,181, issued May 21, 1974.

BACKGROUND OF THE INVENTION

The use of a ninhydrin as a colorimetric reagent for the detection and assay of amino acids, amines and peptides has been known in the art for nearly 60 years. It serves as the basis for the well known Stein-Moore procedure now extensively utilized in the automated assay of amino acids. McCaman and Robins described a fluorometric method for the detection of serum phenylalanine involving the reaction betwen ninhydrin and phenylalanine and discovered the fluorescence was greatly enhanced by the addition of a variety of peptides. Later, Udenfriend and coworkers, Anal. Biochem. 42, 222, 237 (1971), described a fluorometric assay procedure for primary amine-containing compounds, especially peptides and amino acids, which involved the reaction between the primary amine-containing compound, ninhydrin and an aldehyde, preferably phenylacetaldehyde. This procedure was shown to be much more efficient and sensitive than the Stein-Moore and McCaman-Robins procedures.

BRIEF DESCRIPTION OF THE INVENTION

The present invention relates to a novel series of compounds represented by formula I

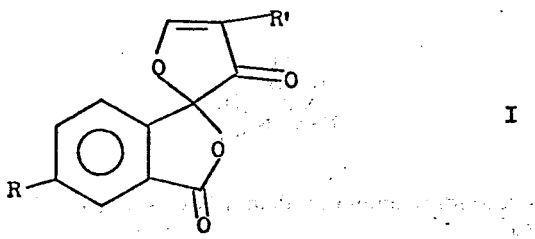

wherein R is hydrogen, halogen, lower alkyl or lower alkoxy and R' is lower alkyl or aryl. These compounds produce highly fluorescent substances upon reaction with primary amine-containing compounds, and are therefore designated as "fluorogens".

In the specification and the appended claims, the term "lower alkyl" shall mean a monovalent, saturated, straight or branched chain hydrocarbon substituent containing up to and including 8 carbon atoms; the term "lower alkoxy" small mean a group having a lower alkyl group linked to an ether oxygen and having its free valence bond from the ether oxygen; the term "aryl" shall mean an aromatic ring system which may be substituted with one or more of the following: halogen (i.e., fluorine, chlorine, bromine or iodine), lower alkyl, lower alkoxy, nitro, cyano and so forth. Exemplary aromatic ring systems include phenyl, naphthyl, furyl, thienyl, pyrrolyl, imidazolyl, pyridyl, pyrimidinyl, indolyl, quinolyl, oxazolyl, isoxazolyl, and so forth.

Preferred compounds of formula I are those where R is hydrogen. Examples of preferred compounds of formula I are:

4-phenylspiro[furan-2(3H), 1'-phthalan]-3,3'-dione 4-(2-methoxyphenyl)spiro[furan-2(3H),1'-phthalan]-3,3'-dione
4-(3-methoxyphenyl)spiro[furan-2(3H),1'-phthalan]-3,3'-dione
4-(4-methoxyphenyl)spiro[furan-2(3H), 1'-phthalan]-3,3'-dione
4-(2,4-dimethoxyphenyl)spiro[furan-2(3H),1'-phthalan]-3,3'-dione
4-(2,5-dimethoxyphenyl)spiro[furan-2(3H),1'-phthalan]-3,3'-dione
4-(3,5-dimethoxyphenyl)spiro[furan-2(3H),1'-phthalan]-3,3'-dione
4-(3,4,5-trimethoxyphenyl)spiro[furan-2(3H),1'-phthalan]-3,3'-dione
4-(2,4,5-trimethoxyphenyl)spiro[furan-2(3H),1'-phthalan]-3,3'-dione
4-(3,4-methylenedioxyphenyl)spiro[furan-2(3H),1'-phthalan]-3,3'-dione
4-(3-chlorophenyl)spiro[furan-2(3H),1'-phthalan]-3,3'-dione
4-(furan--chlorophenyl)spiro[duran-2(3H),1'-phthalan]-3,3'-dione
4-(4-bromophenyl)spiro[furan-2(3H),1'-phthalan]-3,3'-dione
4-(3-indolyl)spiro[furan-2(3H),1'-phthalan]-3,3'-dione
4-(2-naphthyl)spiro[furan-2(3H),1'-phthalan]-3,3'-dione
4-(1-naphthyl)spiro[furan-2(3H),1'-phthalan]-3,3'-dione
4-(1-propyl)spiro[furan-2(3H),1'-phthalan]-3,3'-dione.

Especially preferred is the compound wherein R' is phenyl, i.e. 4-phenylspiro[furan-2(3H),1'-phthalan]-3,3'-dione.

The preparation of compounds of formula I is illustrated in Reaction Scheme A starting from compound II. Compounds of formula II are generally known and are prepared starting with the properly substituted o-acetyl benzoic acid and the desired aldehyde R'CHO. Where particular members of the genus represented by formula II have not been previously described in the art, they may be prepared in the same manner as the known ones.

In the first step, the enol lactone of formula II is hydrolyzed to the keto carboxylic acid of formula III by an aqueous basic hydrolysis, followed by acidification. Suitable bases for the hydrolysis reaction include alkali metal hydroxides, e.g. sodium hydroxide, alkali metal carbonates, e.g. sodium carbonate, and alkali metal bicarbonates, e.g. sodium bicarbonate. A preferred base is an alkali metal hydroxide such as sodium hydroxide. The temperature of the hydrolysis can be in a range of from about 0° to about 100°C. A preferred temperature range is from about 10° to about 40°C. The hydrolysis reaction is suitably performed in an aqueous medium. An organic co-solvent such as a lower alkanol or an organic ether may be employed if desired. At the completion of the reaction, the reaction mixture is acidified to free the carboxylic acid reaction product for the purposes of isolation.

Compounds of formula III are depicted as existing in both the diketo and the enolized form. It should be understood that the ratio of tautomers of the compound may vary depending upon

REACTION SCHEME A

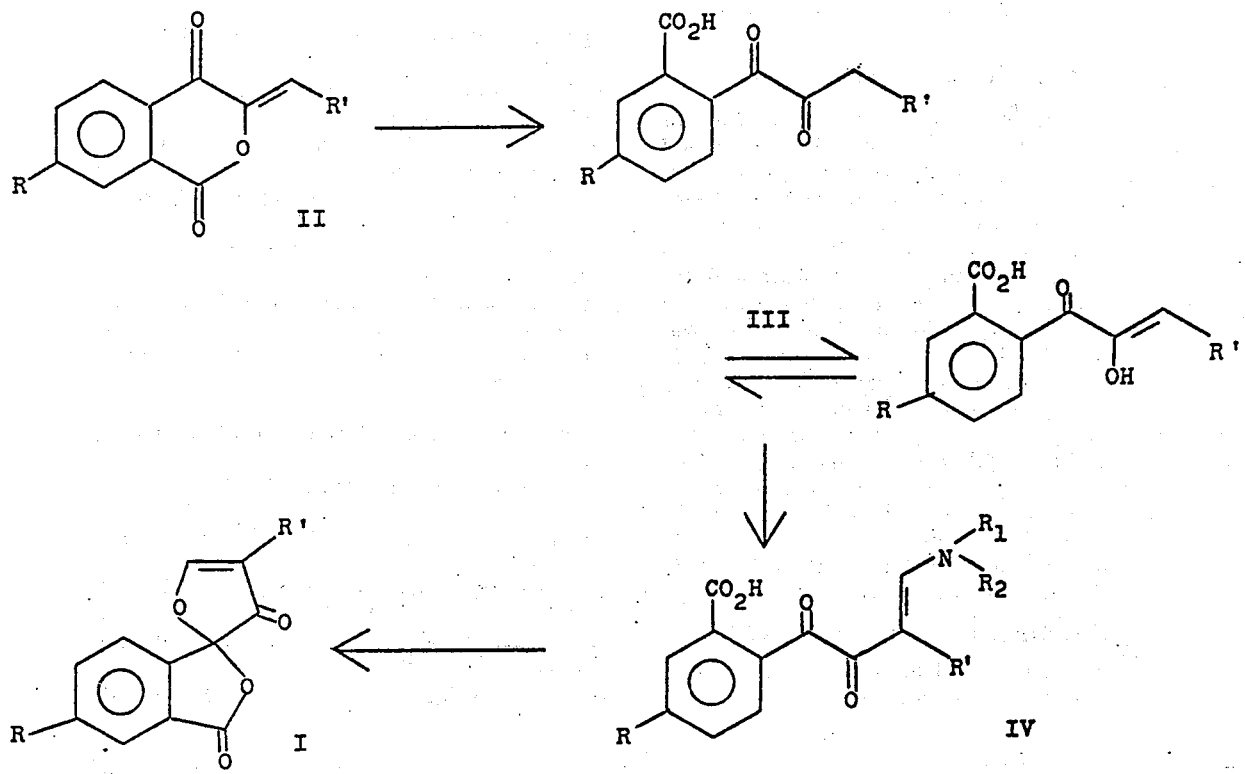

wherein R and R' are as above; $R_1$ and $R_2$ taken independently are each lower alkyl; and $R_1$ and $R_2$ taken together with the nitrogen atom form a 5- or 6-membered saturated heterocyclic ring having at the most 1 additional heteroatom selected from the group consisting of nitrogen and oxygen.

solvent, temperature, pH, and so forth. In the experimental section and the claims, the compounds of formula III are named as the enol form for convenience only.

The keto carboxylic acid of formula III may be converted to the fluorogen of formula I by a two step procedure. In the first step the keto acid of formula III is reacted with an amino-methenylating agent to afford an enamine of formula IV. Suitable amino-methenylating agents include acetals of an N,N-disubstituted formamide, e.g. dimethylformamide dimethylacetal; tris(secondary amino)methanes, e.g. tris(dimethylamino)methane and tris(piperidino) methane; and bis(secondary amino)lower alkoxy methanes, e.g. bis(dimethylamino)-t-butoxy methane.

The amino moiety

as shown in the structural formula for compound IV is introduced from the aminomethenylating agent Acetals of N,N-disubstituted formamides have the general formula,

tris(secondary amino)methanes have the general formula

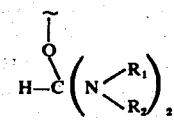

and bis(secondary amino)lower alkoxymethanes have the general formula

Examples of amino moieties $$-N\!\!\diagdown_{R_2}^{R_1}$$

include those where $R_1$ and $R_2$ each taken independently are lower alkyl, e.g. dimethylamino and diethylamino; and those where $R_1$ and $R_2$ taken together with the nitrogen form a 5- or 6-membered heterocyclic ring, e.g. piperidino, morpholino, pyrrolidino, and so forth. This reaction may be carried out in any inert organic solvent. Particularly preferred solvents include formamides, especially dimethylformamide. An excess of aminomethenylating agent may be also utilized as solvent. The preparation of the enamine may be effectuated over a temperature range of from about 0° to about 100°, although a temperature range of from about 10° to about 40° is preferred. A temperature of about room temperature is especially preferred.

The enamine of formula IV may be then directly converted to the fluorogen of formula I by aqueous hydrolysis at a neutral acidic or basic pH. Thus, an acid such as a mineral acid, e.g. HCl; or a weak base such as an alkali metal bicarbonate, e.g. sodium bicarbonate, may be present in the hydrolysis medium. In general, it is preferred to effectuate the aforementioned hydrolysis in the presence of a weak base such as an alkali metal bicarbonate. Upon completion of the hydrolysis and acidification of the reaction medium (in cases, where the hydrolysis is carried out on the neutral or basic side) the desired cyclized fluorogen of formula I is obtained. The temperature of the hydrolysis reaction is suitably in the range of from about 0° to about 100°, although a temperature of about 10° to 40° is preferred. A temperature of about a room temperature is especialy preferred. The conversions II → III, III → IV and IV → I may be carried out with isolation and purification of the product at each stage or, preferably, can be carried out with isolation and purification only of the final fluorogen of formula I.

The fluorogens of formula I react readily with primary amine-containing compounds, particularly with peptides, amino acids and biogenic amines, e.g. catecholamines, to form highly fluorescent materials. Thus, the compounds of formula I serve as highly sensitive reagents for the detection of primary amine-containing compounds. Since the compounds of formula I are stable to aqueous media, the detection of primary amine-containing compounds present in said media is rendered highly practical. This is especially important for the detection of amino acids and peptides which are generally found and analyzed in aqueous media.

The reaction between fluorogens of formula I and primary amine-containing compounds is a rapid and quantitative one. The reaction may be carried out over a wide pH range of from about pH 4 to about pH 11. However, the rate and completeness of the reaction of the fluorogen with the primary amine-containing compounds is optimal within a pH range between about 8 and 9. Thus, reaction of a compound of formula I with a simple primary amine, such as ethylamine, is instantaneously complete at room temperature within this pH range.

It is immediately apparent that the use of a fluorogenic reagent of formula I for the detection of primary amine-containing compounds is superior to the prior art technique hereinabove described involving a ternary reaction between a primary amine-containing compound, ninhydrin and phenylacetaldehyde. A further superiority of the reagents and methods of the present invention is seen from the fact that, in the prior art procedure, it was necessary to heat the mixture of reagents in a temperature of about 60°C. for 15 to 30 minutes to develop maximum fluorescence, whereas, in contradistinction, the reagent of the present invention develops maximum fluorescence instantaneously at room temperature. The fluorescence obtained using equal concentrations of primary amine-containing compounds utilizing the reagents of the present invention is generally in the range of 10 to 50 times greater than that obtained by using the prior art technique.

Thus, the reagents of the present invention may be utilized to detect exceedingly minute quantities of primary amine-containing compounds which was heretofore impossible. Due to the sensitivity of the reagents of the present invention, small amounts of peptides and amino acids can be detected. For example, one can detect and examine quantities of biologically active peptides isolated from a given organ or a single laboratory animal.

The use of the reagents of the present invention for the detection of primary amine-containing compounds may be illustrated in a number of ways. For example, the presence of primary amine-containing compounds in solution may be determined by mixing the sample with an excess of fluorogen of formula I at a desired pH, and measuring the fluorescence. It is preferred to have the primary amine-containing compound in solution in an aqueous medium and to treat it with a solution of the fluorogen in a non-hydroxylic, water miscible solvent such as acetonitrile, dimethylformamide, dimethylsulfoxide, tetrahydrofuran, dioxane; and the like. A 10-fold to 5000-fold molar excess of fluorogen is preferred. A 50-fold to 1000-fold molar excess is especially preferred.

Alternatively, the fluorogens of the present invention may be utilized to detect the presence of primary amine-containing compounds, especially amino acids, on paper or thin-layer chromatographic systems. In such a technique, the reagent in a solvent, preferably a volatile organic solvent, optionally containing a pH buffer, is applied to the chromatographic system, usually as a spray, and the paper or thin-layer chromatogram is examined under a fluorescent light source. The development of fluorescence is instantaneous at room temperature and, thus, there is no need to heat the chromatogram to develop fluorescence. This offers a decided advantage over prior art techniques.

Another application of the fluorogens of the present invention is the use in automated analysis of amino acids. In such a procedure, a sample stream which is a portion of the effluent of a chromatographic column is mixed with the fluorogenic reagent of formula I at the desired pH and the mixture immediately analyzed by a spectrofluorometer. In this manner, a monitoring of the fluorescence exhibited by a continuous sample stream is indicative of the presence and concentration of various amino acids.

A further appreciation of the preparation of the novel fluorogens of the present invention and their use in producing highly fluorescent substances upon reaction with primary amine-containing compounds may be obtained from the following examples.

EXAMPLE 1 1,4A solution of 8.1 g., 1.4-isochromandione (0.05 mole), 6.0 g. benzaldehyde (0.055 mole) and 0.1 ml. piperidine in 50 ml. benzene was heated at reflux temperature under nitrogen until the theoretical amount of water (0.05 mole) had collected in a Dean-Stark trap (ca. 2 hrs.). The reaction mixture was then cooled to 10° and the product was filtered off. The filter cake was recrystallized from benzene to afford 11.4 g., 3-benzylidene-4-keto-3,4-dihydroisocoumarin, m.p. 117°.

Anal. Calcd. for $C_{16}H_{10}O_3$: C, 76.79; H, 4.03. Found: C, 76.49; H, 4.05.

Analogously were prepared from 1,4-chromandione and the corresponding aldehydes the compounds listed in Table I:

Table I

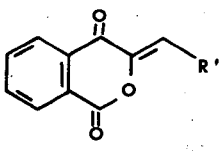

| R'= | mp | Empirical Formula | Analysis Calcd. | Found |
|---|---|---|---|---|
| 2-methoxyphenyl | 200° | C₁₇H₁₂O₄ | C,72.85 H, 4.32 | 72.96 4.19 |
| 3-methoxyphenyl | 153° | C₁₇H₁₂O₄ | C,72.85 H, 4.32 | 72.52 4.21 |
| 4-methoxyphenyl | 200° | C₁₇H₁₂O₄ | C,72.85 H, 4.32 | 72.56 4.29 |
| 2,4-dimethoxyphenyl | 201° | C₁₈H₁₄O₅ | C,69.67 H, 4.55 | 69.53 4.57 |
| 2,5-dimethoxyphenyl | 160° | C₁₈H₁₄O₅ | C,69.67 H, 4.55 | 69.65 4.54 |
| 3,5-dimethoxyphenyl | 178° | C₁₈H₁₄O₅ | C,69.67 H, 4.55 | 69.62 4.63 |
| 3,4,5-trimethoxyphenyl | 144° | C₁₉H₁₆O₆ | C,67.05 H, 4.75 | 66.71 4.56 |
| 2,4,5-trimethoxyphenyl | 210° | C₁₉H₁₆O₆ | C,67.05 H, 4.75 | 67.35 4.77 |
| 3,4-methoxylenedioxyphenyl | 226° | C₁₇H₁₀O₅ | C,69.39 H, 3.43 | 69.16 3.33 |
| 3-chlorophenyl | 224° | C₁₆H₉ClO₃ | C,67.50 H, 3.19 | 67.41 3.21 |
| 4-chlorophenyl | 203° | C₁₆H₉ClO₃ | C,67.50 H, 3.19 | 67.26 3.04 |
| 4-bromophenyl | 204° | C₁₆H₉BrO₃ | C,58.38 H, 2.76 | 58.46 2.66 |
| 3-indolyl | 308° | C₁₈H₁₁NO₃ | C,74.73 H, 3.83 N,4.84 | 74.69 3.94 4.92 |
| 2-naphthyl | 251° | C₂₀H₁₂O₃ | C,79.99 H, 4.03 | 80.28 4.01 |
| 1-naphthyl | 184° | C₂₀H₁₂O₃ | C,79.99 H, 4.03 | 80.27 3.95 |
| n-propyl | 58° | C₁₃H₁₂O₃ | C,72.21 H, 5.59 | 72.01 5.44 |

EXAMPLE 2

To a solution of 20 g. 3-benzylidene-4-keto-3,4-dihydroisocoumarin in 400 ml. methanol was added 100 ml. 1N aqueous sodium hydroxide. The mixture was stirred at room temperature for 30 minutes. It was then diluted with water and acidified with 10% hydrochloric acid. The precipitating o-(α-hydroxycinnamoyl) benzoic acid was extracted twice with chloroform. The organic extracts were washed with water, dried over sodium sulfate and evaporated under reduced pressure to dryness. The residue was dissolved in 80 ml. dimethylformamide. The solution was cooled to 0°, and, while stirring, 24 ml. tris(dimethylamino)methane were added. Stirring was continued at room temperature for 60 minutes. The 1-dimethylamino-2-phenyl-4(o-carboxyphenyl)-1-buten-3,4-dione which had formed was not isolated, but rather, the DMF-solution was poured into ice-water. The resultant aqueous alkaline solution was extracted with ether. The ether extract was discarded and the aqueous layer was acidified with dilute hydrochloric acid. The desired 4-phenylspiro[furan-2(3H)-1-phthalan]3,3'-dione was extracted 3 times with ether/ benzene (1:1). The combined extracts were dried over sodium sulfate and evaporated under reduced pressure. The crystalline residue was resuspended in ether and filtered off to give 12.0 G. pure material, mp 153°.

Anal. Calcd. for C₁₇H₁₀O₄: C, 73.38; H, 3.62. Found: C, 73.41; H, 3.57

The compounds listed in Table II were prepared by analogous procedures, starting with the appropriate 3-arylidene- or 3-alkylidene-4-keto-3,4-dihydroisocoumarins, prepared as in Example 1.

Table II

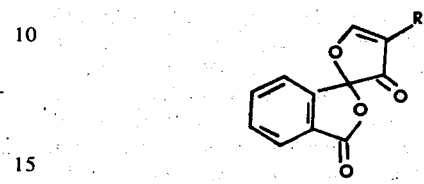

| R'= | mp | Empirical formula | Analysis Calcd. | Found |
|---|---|---|---|---|
| 2-methoxyphenyl | 153° | C₁₈H₁₂O₅ | C,70.13 H, 3.92 | 70.24 3.86 |
| 3-methoxyphenyl | 118° | C₁₈H₁₂O₅ | C,70.13 H, 3.92 | 70.13 3.71 |
| 4-methoxyphenyl | 158° | C₁₈H₁₂O₅ | C,70.13 H, 3.92 | 70.40 4.01 |
| 2,4-dimethoxyphenyl | 133° | C₁₉H₁₄O₆ | C,67.45 H, 4.17 | 67.21 4.06 |
| 2,5-dimethoxyphenyl | 148° | C₁₉H₁₄O₆ | C,67.45 H, 4.17 | 67.54 4.09 |
| 3,5-dimethoxyphenyl | 138° | C₁₉H₁₄O₆ | C,67.45 H, 4.17 | 67.72 3.98 |
| 3,4,5-trimethoxyphenyl | 205° | C₂₀H₁₆O₂ | C,65.21 H, 4.38 | 65.33 4.26 |
| 2,4,5-trimethoxyphenyl | 179° | C₂₀H₁₆O₇ | C,65.21 H, 4.38 | 65.34 4.27 |
| 3,4-methylenedioxyphenyl | 195° | C₁₈H₁₀O₆ | C,67.08 H, 3.13 | 67.08 3.43 |
| 3-chlorphenyl | 144° | C₁₇H₉ClO₄ | C,65.30 H, 2.90 | 65.32 2.61 |
| 4-chlorophenyl | 167° | C₁₇H₉ClO₄ | C,65,30 H, 2.90 | 65.10 2.92 |
| 4-bromophenyl | 181° | C₁₇H₉BrO₄ | C,57.17 H, 2.54 | 57.25 2.63 |
| 3-indolyl | 186° | C₁₉H₁₁NO₄ | C,71.92 N, 3.49 N,4.41 | 72.16 3.43 4.16 |
| 2-naphthyl | 170° | C₂₁H₁₂O₄ | C,76.82 H, 3.68 | 76.62 3.58 |
| 1-naphthyl | 191° | C₂₁H₁₂O₄ | C,76.82 H, 3.68 | 76.85 3.53 |
| n-propyl | Oil | C₁₄H₁₂O₄ | | |

EXAMPLE 3

To a suspension of 2.5 g. 3-benzylidene-4-keto-3,4-dihydroisocoumarin in 50 ml. methanol were added 10 ml. of 1N aqueous sodium hydroxide. The mixture was stirred at room temperature for 1 hour. A dark red solution resulted. The solution was diluted with water, acidified with 10 ml. of 1N hydrochloric acid and extracted 3 times with methylene chloride. The organic extracts were combined, washed with water, dried over sodium sulfate, and evaporated in vacuo at 20°–30°. The residue was dissolved in methylene chloride at room temperature. Petroleum ether was added to the solution to the point of incipient turbidity. The resulting mixture was kept at room temperature for 16 hours, after which time the desired acid had crystallized and was filtered off. The crystals were washed on the filter with methylene chloride/ petroleum ether (1:9) and dried in vacuo to afford 2.0 g. of o-(α-hydroxycinnamoyl)benzoic acid, mp 99°–105°.

The compounds listed in Table III were prepared by analogous procedures, starting with the appropriate 3-arylidene-4-keto-3,4-dihydroisocoumarins, prepared as in Example 1.

Table III

[Structure: benzene ring with HO₂C and C(=O)-C(OH)=CH-R' substituents ortho]

| R'= | mp | Empirical Formula | Analysis Calcd. | Found |
|---|---|---|---|---|
| 2-methoxyphenyl | 131–136° | $C_{17}H_{14}O_5$ | C, 68.45<br>C, 4.73 | 68.14<br>4.73 |
| 3-methoxyphenyl | 133–135° | $C_{17}H_{14}O_5$ | C, 68.45<br>H, 4.73 | 68.75<br>5.00 |
| 4-methoxyphenyl | 117–123° | $C_{17}H_{14}O_5$ | C, 68.45<br>H, 4.73 | 68.52<br>4.78 |
| 2,5-dimethoxyphenyl | 131–132° | $C_{18}H_{16}O_6$ | C, 65.85<br>H, 4.91 | 65.82<br>5.20 |
| 3,5-dimethoxyphenyl | 131–134° | $C_{18}H_{16}O_6$ | C, 65.85<br>H, 4.91 | 66.08<br>5.03 |
| 2,4,5-trimethoxyphenyl | 152–165° | $C_{19}H_{18}O_7$ | C, 63.68<br>H, 5.06 | 63.33<br>5.11 |
| 3-chlorophenyl | 117–118° | $C_{16}H_{11}ClO_4$ | C, 63.48<br>H, 3.66 | 63.59<br>3.63 |
| 4-bromophenyl | 130–132° | $C_{16}H_{11}BrO_4$ | C, 55.35<br>H, 3.19 | 55.37<br>3.24 |
| 3-indolyl | 120–125° | $C_{18}H_{13}NO_4 \cdot ½$ | C, 63.52<br>H, 4.03<br>N, 4.01 | 63.63<br>3.78<br>3.94 |
| 1-naphthyl | 154–160° | $C_{20}H_{14}O_4$ | C, 75.46<br>H, 4.43 | 75.53<br>4.61 |

EXAMPLE 4

To a solution of 268 mg. o-(α-hydroxycinnamoyl)-benzoic acid in 5 ml. of dimethylformamide were added 2 ml. dimethylformamide dimethyl acetal. The reaction mixture was kept at room temperature for 17 hours. The solution containing 1-dimethylamino-2-phenyl-4(o-carboxyphenyl)-1-buten-3,4-dione was then poured into water, acidified with dilute hydrochloric acid and extracted with methylene chloride. The organic extract was dried over sodium sulfate and concentrated in vacuo. The concentrate was applied to a short silica gel column (4.5 g.) and eluted with methylene chloride. The eluate was evaporated in vacuo and the residue was was recrystallized from methylene chloride/ether. There were obtained 110 mg. 4-phenylspiro[furan-2(3H),1'-phthalan]3,3'-dione, mp 151°–154°.

EXAMPLE 5

To a solution of 12.5 g. 3-benzylidene-4-keto-3,4-dihdyroisocoumarin in 200 ml. methanol were added 50 ml. of 1N aqueous sodium hydroxide. The reaction mixture was stirred at room temperature for 90 minutes. It was then poured onto ice. The resulting aqueous mixture was acidified with 50 ml. of 1N hydrochloric acid and extracted 4 times with methylene chloride. The extracts were combined, dried over sodium sulfate and evaporated in vacuo. The residue containing o-(α-hydroxycinnamoyl)benzoic acid was dissolved in 150 ml. dimethylformamide. To this solution were added 30 g. tris(piperidino)methane. The mixture was stirred at room temperature for 5 hours and the solution containing 1-(1-piperidino)-2-phenyl-4-(o-carboxyphenyl)-1-buten-3,4-dione then poured into ice-water. The alkaline aqueous mixture was extracted with ether. The ether extract was discarded. The aqueous layer was acidified with 1N hydrochloric acid (300 ml.) and extracted 4 times with methylene chloride. The organic extracts were combined, washed with water, dried over sodium sulfate and evaporated to dryness under reduced pressure. The residue was dissolved in 75 ml. methylene chloride and treated with 1 g. of Norite at reflux temperature. The hot solution was filtered. The filtrate was concentrated to 50 ml. and then diluted with 100 ml. ether. From the mixture there crystallized 8.4 g. of 4-phenylspiro[furan-2(3H),1'-phthalan]-3,3'-dione; mp 151°–153°.

The compounds listed in Table II were prepared by analogous procedures, starting with the appropriate 3-arylidene- or 3-alkylidene-4-keto-3,4-dihydroisocoumarins prepared as in Example 1.

EXAMPLE 6

To a solution of 4.47 g. o(α-hydroxy-2-methoxycinnamoyl) benzoic acid in 30 ml. dimethylformamide were added 5 g. tris-(dimethylamino)-methane. The mixture was stirred at room temperature for 3½ hours. Most of the excess formylating agent and the solvent were then removed under reduced pressure at 55°–60°. The residue containing 1-dimethylamino-2-(o-methoxyphenyl)-4-(o-carboxyphenyl)-1-buten-3,4-dione was redissolved in 10 ml. of dimethylformamide and this solution added to 100 ml. water. The resulting alkaline mixture was extracted with methylene chloride. The organic extract was discarded. The aqueous layer was acidified with dilute hydrochloric acid and extracted twice with methylene chloride. The organic phases were combined, washed with water, dried over sodium sulfate and evaporated to dryness under reduced pressure. The remaining oil was dissolved in ether. Crystals precipitated from the ether solution upon refrigeration. They were collected by filtration to afford 2.4 g. 4-(2-methoxyphenyl) spiro[furan-2(3H),1'-phthalan]-3,3'-dione, mp 152°–154°.

The compounds listed in Table III were converted to the corresponding spirolactones listed in Table II by analogous procedures.

EXAMPLE 7

Fluorometric Assay

Procedure:

Place in a test tube:
a. 1 ml. of peptide solution (20 nanomole leucyl-alanine in 1 ml. pH 8-phosphate buffer) and
b. 2 ml. pH 8-buffer solution (Fisher). While agitating with a vibro-mixer add rapidly:
c. 1 ml. of reagent solution (containing 0.2 millimole of spirolactone of Table II in 100 ml. acetonitrile).

Final concentrations:
Leu-ala: 5 nanomole/ml
reagent: 0.5 μmole/ml (100 fold excess)
acetonitrile: 25%
aqueous buffer: 75%

Measure fluorescence immediately.

Instrumentation:
Farrand Spectrofluorometer
Excitation: 390 nm; slits 10,10
Emission: 385 nm; slits 20,20
Sensitivity = 1

Results:

With 4-phenylspiro[furan-2(3H),1'-phthalan]3,3'-dione as the reagent a fluorescent intensity of 80, relative to a fluorescence intensity of 70 (at the same excitation and emission settings) for a quinine standard, 10 mg/ml 0.01N $H_2SO_4$ was observed.

The above experiment was repeated using ethylamine in place of leucylalanine, and ethanol in place of acetonitrile. The fluorescence intensity obtained by utilizing various spirolactone reagents of Table II is shown in Table IV. The fluorescence intensity obtained using 4-phenylspiro[furan-2(3H),1'-phthalan]3,3'-dione has been arbitrarily assigned the value 100, and the other intensities are given relative to it.

Table IV

| Compound of Table II R'= | λmax. EX | λmax. Em | Rel. Fluorescence Intensity |
|---|---|---|---|
| phenyl | 390 | 475 | 100 |
| 3-methoxyphenyl | 391 | 475 | 115 |
| 4-methoxyphenyl | 395 | 495 | 110 |
| 3,5-dimethoxyphenyl | 390 | 475 | 120 |
| 4-chlorophenyl | 390 | 475 | 110 |
| 1-naphthyl | 310 | 483 | 94 |
| 3,4,5-trimethoxyphenyl | 390 | 475 | 60 |
| n-propyl | 370 | 445 | 47 |

EXAMPLE 8

Starting with the appropriate 5-substituted-2-acetylbenzoic acids, and proceeding, first according to known procedures, to the corresponding 7-substituted-1,4-isochromandione, and then, according to the procedure of Example 1, to the 7-substituted-3-benzylidene-4-keto-3,4-dihydroisocoumarin, the following series of intermediates and fluorogens were prepared, following the procedures of Example 2:

3-benzylidene-4-keto-7-methyl-3,4-dihydroisocoumarin,
2-(α-hydroxycinnamoyl)-5-methyl-benzoic acid,
1-dimethylamino-2-phenyl-4(2-carboxy-4-methylphenyl)-1-buten-3,4-dione,
5'-methyl-4-phenylspiro[furan-2(3H),1'-phthalan]-3,3'-dione,
3-benzylidene-4-keto-7-butyl-3,4-dihydroisocoumarin,
2-(α-hydroxycinnamoyl)-5-butyl-benzoic acid,
1-dimethylamino-2-phenyl-4(2-carboxy-4-butylphenyl)-1-buten-3,4-dione,
5'-butyl-4-phenylspiro[furan-2(3H),1'-phthalan]-3,3'-dione,
3-benzylidene-4-keto-7-methoxy-3,4-dihydroisocoumarin,
2-(α-hydroxycinnamoyl)-5-methoxy-benzoic acid,
1-dimethylamino-2-phenyl-4(2-carboxy-4-methoxyphenyl)-1-buten-3,4-dione,
5'-methoxy-4-phenylspiro[furan-2(3H),1'-phthalan]-3,3'-dione,
3-benzylidene-4-keto-7-chloro-3,4-dihydroisocoumarin,
2-(α-hydroxycinnamoyl)-5-chloro-benzoic acid,
1-dimethylamino-2-phenyl-4(2-carboxy-4-chlorophenyl)-1-buten-3,4-dione,
5'-chloro-4-phenylspiro[furan-2(3H),1'-phthalan]-3,3'-dione.

We claim:
1. A process for preparing a compound of the formula

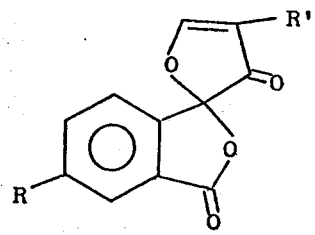

wherein R is hydrogen, halogen, lower alkyl or lower alkoxy and R' is lower alkyl or aryl, which comprises contacting a compound of the formula

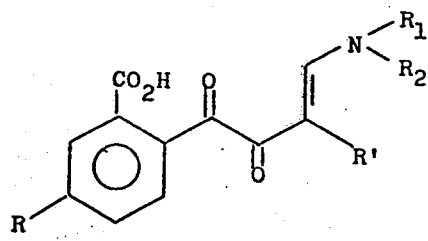

wherein R and R' are as above and $R_1$ and $R_2$ taken independently are each lower alkyl and $R_1$ and $R_2$ taken together with the nitrogen atom form a 5- or 6-membered saturated heterocyclic ring having at the most one additional heteroatom selected from the group consisting of nitrogen and oxygen, with an aqueous medium.

2. The process of claim 1 wherein an acid or base is present in the aqueous medium.

3. The process of claim 2 wherein the base is an alkali metal bicarbonate.

4. The process of claim 1 wherein the temperature is from about 10° to about 40°C.

* * * * *